United States Patent [19]
Fletcher et al.

[11] 3,972,038
[45] July 27, 1976

[54] ACCELEROMETER TELEMETRY SYSTEM

[76] Inventors: James C. Fletcher, Administrator of the National Aeronautics and Space Administration, with respect to an invention of; Eph Konigsberg, Sierra Madre, Calif.

[22] Filed: Mar. 28, 1975

[21] Appl. No.: 563,049

[52] U.S. Cl. .............................. 340/189 M; 73/493; 73/517 R; 340/206
[51] Int. Cl.² ......................................... G08C 19/16
[58] Field of Search .......... 340/189 M, 206; 73/493, 73/517 R

[56] References Cited
UNITED STATES PATENTS

| | | | |
|---|---|---|---|
| 3,247,497 | 4/1966 | Lee | 340/206 |
| 3,350,944 | 11/1967 | Michele | 340/189 M |
| 3,717,857 | 2/1973 | Evans | 340/189 M |

*Primary Examiner*—Thomas B. Habecker
*Attorney, Agent, or Firm*—Darrell G. Brekke; Armand G. Morin, Sr.; John R. Manning

[57] ABSTRACT

An accelerometer telemetry system incorporated in a finger ring is used for monitoring the motor responses of a subject. The system includes an accelerometer, battery and transmitter and provides information to a remote receiver regarding hand movements of a subject wearing the ring, without the constraints of wires. Possible applications include the detection of fatigue from the hand movements of the wearer.

6 Claims, 14 Drawing Figures

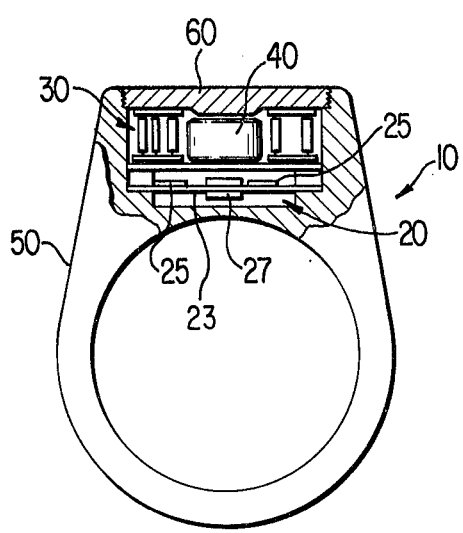
FIG. 1
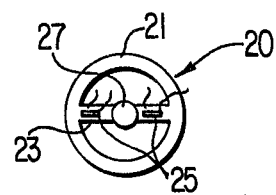
FIG. 2a
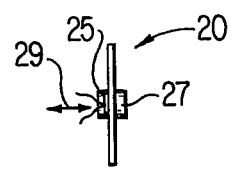
FIG. 2b
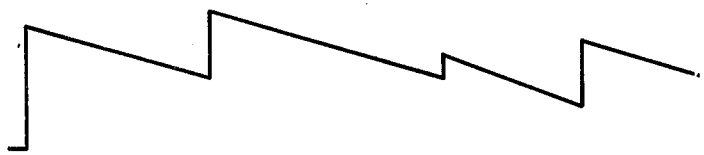
FIG. 8a — VOLTAGE ACROSS C5
FIG. 8b — PULSE TURN-ON
FIG. 8c — STRAIN GAGE ACTIVATION
FIG. 8d — RF OUTPUT

ACCELEROMETER TELEMETRY SYSTEM

ORIGIN

The invention described herein was made in the performance of work under a NASA contract and is subject to the provisions of Section 305 of the National Aeronautics and Space Act of 1958, Public Law 85–568 (72 Stat. 435; 42 U.S.C. 2457).

FIELD OF THE INVENTION

This invention relates to accelerometer telemetry systems, and, more particularly, to a self-contained miniaturized accelerometer telemetry system incorporated finger ring, used in monitoring of the motor responses of the ring wearer.

BACKGROUND OF THE INVENTION

In certain critical activities, such as the piloting of an aircraft or activities involved with flight control, it is desirable to determine when the operator performing these activities is becoming fatigued. Such fatigue, which may be physical or psychological, can, of course, have a serious effect on the judgment and/or reaction speed of the operator. Studies have shown that an individual's motor activities, as evidenced by hand tremor and other hand motions, change in relation to degree of fatigue. Information regarding hand motions can be obtained in a number of known ways, but such information is obviously most reliable and thus useful when gathered without interfering with the normal routine of the subject. Thus, massive, bulky systems as well as systems requiring wires or other direct interconnections with a subject have limited application in situations where the presence of a sensing device or interconnecting wires would curtail normal activities or otherwise affect the results obtained.

SUMMARY OF THE INVENTION

According to the present invention, a miniaturized telemetry system is provided which continuously monitors the hand movements of a subject and transmits the resultant information to a remote receiver. The telemetry system includes a miniaturized semiconductor strain gage coupled to a seismic mass for detecting the movements in question and for producing an electrical output signal in accordance therewith. The strain gages are preferably activated by short duration pulses, rather than continuous activation, so as to conserve power. The output signal is used to modulate the time interval between output pulses of a radio frequency transmitter. The entire sensing and transmitting package, including a power source, is contained in a case or housing the size and shape of a finger ring, thus permitting a subject to "wear" the system and perform his normal routine of tasks without interference therefrom.

The modulated radio frequency transmission is received and demodulated by known techniques, and the resultant information is made available for recording or display. Records can be made over a period of time during normal activities in order to determine a "normal" level of hand accelerations. After a standard is developed for a particular subject, analysis of working conditions and variations from the standard can indicate various levels of fatigue.

Other features and advantages of the invention will be set forth in, or apparent from, the detailed description of a preferred embodiment found hereinbelow.

BRIEF DESCRIPTION OF THE DRAWINGS

FIG. 1 is a side elevational view, partially in section, of a preferred embodiment of an accelerometer telemetry system in accordance with the invention;

FIG. 2a is a plan view of a preferred embodiment of the accelerometer of FIG. 1;

FIG. 2b is an end elevational view of the accelerometer in FIG. 2a;

FIG. 4b is a plan view of the accelerometer in FIG. 4a;

FIGS. 8a, 8b, 8c, and 8d are waveform diagrams associated with the circuit in FIG. 4.

DESCRIPTION OF THE PREFERRED EMBODIMENT

Figure 3A:
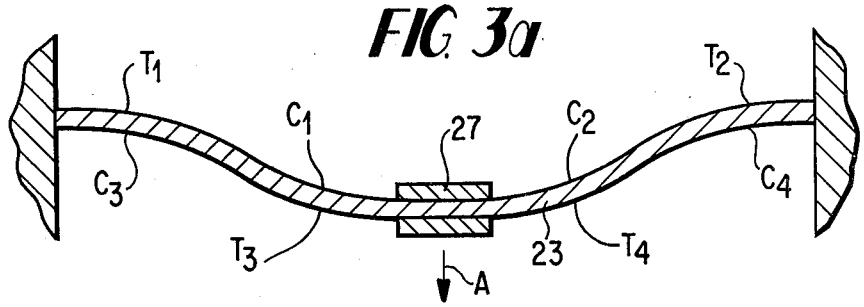
FIGS. 3a and 3b are diagrams of the accelerometer in FIG. 2a showing the compressional and tension zones resulting from movement of the seismic mass.

Referring to FIG. 1, a self-contained accelerometer telemetry system, generally denoted 10, is illustrated. The system basically comprises an accelerometer 20, a transmitter 30 and a battery 40 all packaged in a casing or housing, 50 which is the size and shape of a finger ring. A cover 60 is screwed into an upper opening in ring housing 50 so as to completely enclose the system electronics therein.

Accelerometer 20 is shown in greater detail in FIGS. 2a and 2b and, as illustrated, includes a chemically etched ring 21 and a central beam 23, the latter of which supports a centrally located seismic mass 27. Affixed to beam 23 of accelerometer 20, on either side of seismic mass 27, are first and second semiconductor gages 25. Movements of seismic mass 27, indicated by arrow 29, are converted into stresses in beam 23, these stresses being detected by strain gages 25 and converted into corresponding electrical signals. The resistances of strain gages 25 are directly proportional to detected stresses, so that a current passing through the gages will produce a voltage proportional to the detected stresses according to the formula $\Delta E = I \Delta R$, where $\Delta E$ is a voltage change, $I$ is the current and $\Delta R$ is the change in resistance of strain gages 25. The use of a constant current $I$ is preferred but is not necessary for the circuit to function properly.

Figure 3B:
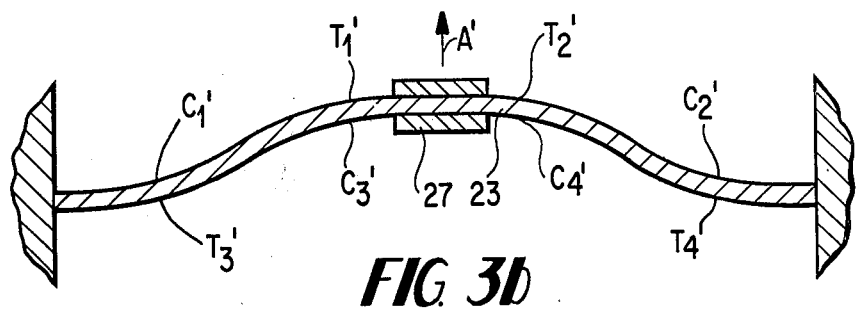
Figure 4A:
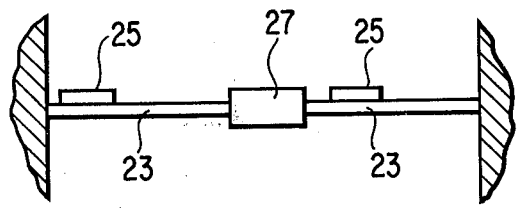
FIG. 4a is a side elevational view of the accelerometer in FIG. 2a showing the positioning of the strain gages.
Figure 4B:
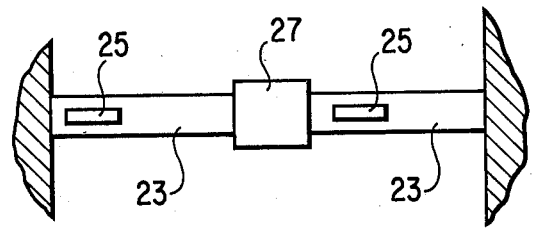

Beam 23, on which strain gages 25 are mounted, is a double-clamped beam, that is, the beam 23 is fixed at both ends. In order for a voltage divider strain gage circuit, shown in FIG. 7 and described hereinbelow, to function properly, one strain gage 25 must be in compression while the other strain gage 25 is in tension. This tension/compression relationship is achieved in the prior art by positioning strain gages 25 orthogonally, with one gage parallel to the longitudinal beam axis and the other perpendicular to that beam axis. However, the narrow width of beam 23 precludes such an arrangement. As shown in FIG. 3a, the double clamped beam 23 has four compressional zones, denoted $C_1$, $C_2$, $C_3$, and $C_4$, and four tension zones, denotes $T_1$, $T_2$, $T_3$, and $T_4$, when seismic mass 27 moves in the direction of arrow A. Similarly, as shown in FIG. 3b, beam 23 has four compressional zones $C_1'$, $C_2'$, $C_3'$, and $C_4'$ and four tension zones $T_1'$, $T_2'$, $T_3'$, and $T_4'$ when seismic mass 27 moves in the direction of arrrow A'. It will be appreciated that a compression zone changes to a tension zone when seismic mass 27 moves from one extreme position to the other ($C_1$ changes to $T_1'$, $C_2$ changes to $T_2'$, etc.). Thus, the desired tension/compression placement is achieved by positioning strain gages 25 as shown in FIGS. 4a and 4b.

The electrical signals resulting from the changes in the resistances of strain gages 25 form the inputs to transmitter 30 in FIG. 1. Referring to the schematic block diagram in FIG. 5, the principal components of the transmitter 30 are shown. The transmitter includes an astable multivibrator 75 which provides pulses to energize accelerometer 20, as well as to activate a sample-and-hold circuit 70 and to gate an RF oscillator 85, which provides a frequency, for example, in the FM band (88–108MHz), and which feeds an output antenna 87. Transmitted RF bursts of constant width and amplitude are time modulated in accordance with the resistance changes produced by accelerometer 20. By using bursts rather than continuous transmission, a low duty factor is realized and power is conserved. The overall operation of transmitter 30 is described hereinbelow.

Figure 5:
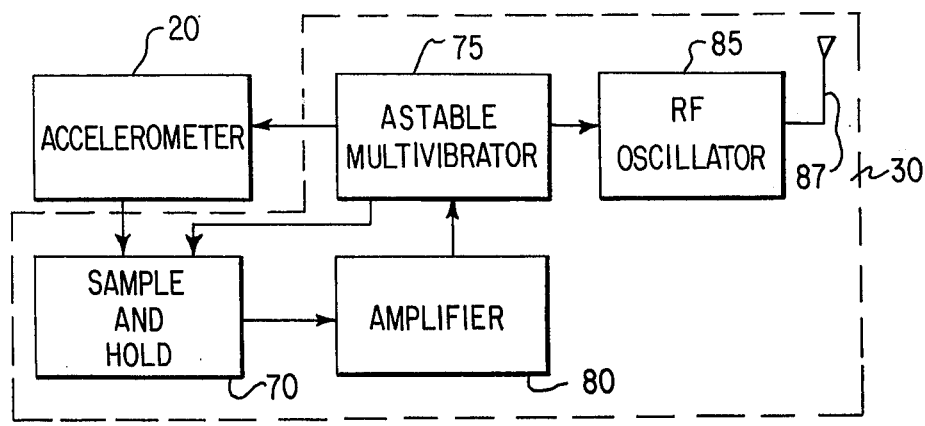
FIG. 5 is a block form schematic circuit diagram of the accelerometer telemetry system of FIG. 1.
Figure 6:
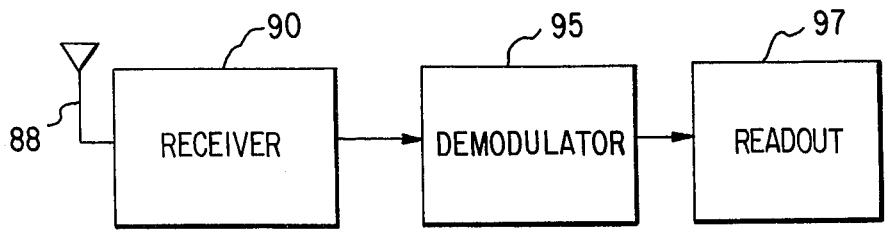
FIG. 6 is a block form schematic circuit diagram of a remote receiver suitable for use in the telemetry system of the invention.

Referring to FIG. 6, the time-modulated RF bursts transmitted by antenna 87 of FIG. 5 are received by a receiver antenna 88. A telemetry receiver 90 of conventional design generates a single pulse for each RF burst received. A demodulator 95, which is also of known design, converts the pulse train at the output of receiver 90 into an analog signal representing hand accelerations as reflected by the movements of seismic mass 27. This analog signal is recorded or displayed by conventional recording or display devices, represented by readout 97, for analysis and comparison to a standard established for a particular subject. The telemetry receiver 92 can be, for example, a Konigsberg Instruments Model TR1-2 while the demodulator 95 can be a single channel demodulator similar to that described in Fryer, "Implantable Biotelemetry Systems," NASA Publication SP-5094, 1970. Readout 97 can be, for example, a meter, a pen recorder, a tape recorder, or an oscilloscope.

Figure 7:
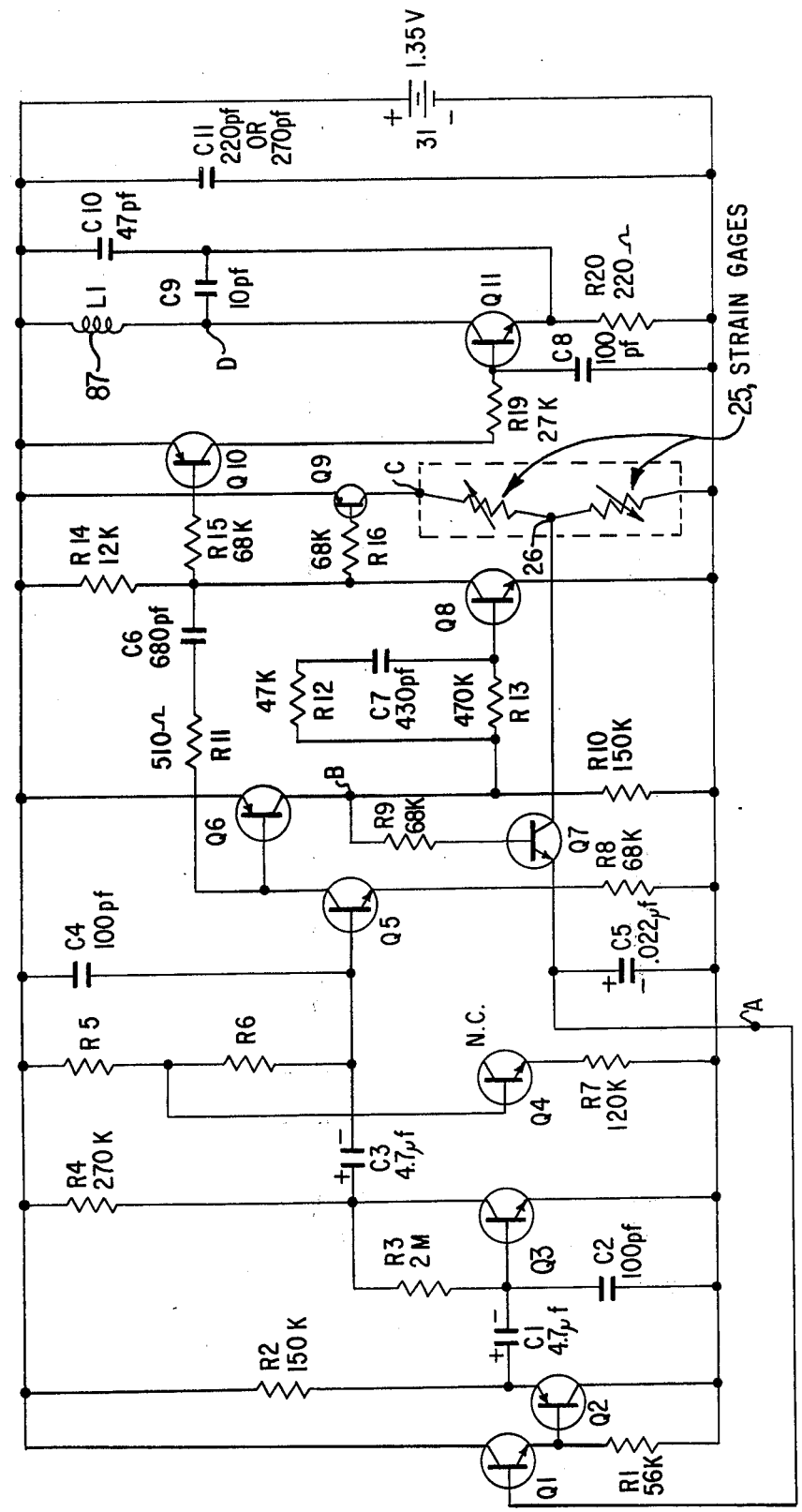
FIG. 7 is a schematic circuit diagram of the accelerometer and transmitter of FIG. 3.

Referring now to FIG. 7, a schematic circuit diagram of transmitter 30 of FIG. 5 is shown. Although FIG. 7 depicts transmitter 30 having discrete components, it is to be understood that the transmitter could even be made smaller by utilizing integrated circuitry.

The transmitter circuit of FIG. 7 provides for sampling the resistance of strain gages 25 using a pulsed input. The voltage resulting at point 26, which is derived in a manner described in greater detail hereinbelow, passes through transistor Q7 during the sampling period and is stored by capacitor C5. Thus, the charge on C5 will be reflective of the results of the previous sampling of strain gages 25. The voltage present on capacitor C5 is tracked by a high impedance follower formed by transistors Q1, Q2 and resistors R1 and R2 connected as shown. A capacitor C1 couples the output of the high impedance follower to a signal amplifier comprising capacitors C3, R3, R4 and a transistor Q3, the signal amplifier providing a gain or approximately five. Capacitor C1 provides a coupling cutoff frequency of approximately 0.4 Hz, which is adequate for the detection of even slow movements. A transistor Q4, and resistors R5, R6, and R7 provide temperature compensation for a transistor Q5, which transistor generates a constant current output that varies with the signal coming from the preceding amplifier stage. A capacitor C6 connected to the collector of transistor Q5 charges through resistors R11 and R14 until a further transistor Q6, coupled to the collector of transistor Q5, is turned on. Current through transistor Q6 switches on a further transistor Q7 which is connected to the collector thereof through a resistor R9.

The collector of transistor Q7 is connected to a point on the junction between strain gage resistors 25 of accelerometer 20 while the collector of transistor Q6 is also connected to the base of a transistor Q8 through a network comprising a capacitor C7 and two resistors R12 and R13. As illustrated, the collector of transistor Q8 is connected to the base terminals of two further transistors Q9 and Q10. Thus, transistors Q6 and Q8 form an astable multivibrator, and when transistor Q8 is switched on, transistors Q9 and Q10 also switch on through their base resistors R15 and R16. Transistor Q8 will remain on until capacitor C7 charges up, whereupon transistor Q8 will turn off and reset the cycle. The "on" time of transistor Q8 is determined by the time constant of resistors R12, R13 and capacitor C7 and is approximately between 25 and 35 microseconds for the component values shown in FIG. 7. Thus, a constant width pulse is produced by the astable multivibrator transistor pair Q6 and Q8. The interval between pulses is determined by the charging of capacitor C6, which is controlled by current generator transistor Q5. The output of transistor Q5 is determined, as described hereinabove, by the charge on capacitor C5, which varies with the resistance of accelerometer strain gages 25.

When transistor Q9 is turned on the a fixed length of time by transistor Q8, strain gages 25 are activated. The voltage at point 26 is determined by the divider network formed by the resistances in strain gages 25. Thus, during the turn-on time of transistor Q9, the voltage at 26 reflects the position of seismic mass 27. Since transistor Q7 is also turned on at this time, the resulting voltage at 26 is stored by capacitor C5 and that voltage will determine the time interval until the next pulse, as described hereinabove. When transistor Q10 is turned on by transistor Q8 during a pulse, a radio frequency oscillator and transmitter, made up of resistors R19, R20, capacitors C8, C9, C10 and transistor Q11, produce an RF output across coil L1. Coil L1 serves a dual purpose, being both the inductive element in the oscillator tank circuit and the RF radiator (transmitting antenna 87). Power for the circuitry is supplied by a 1.35-volt miniature mercury battery. Capacitor C11, connected across the terminals of the battery, serves as an RF bypass.

Thus, to briefly summarize the operation, a pulsing voltage activates the strain gages, a switching circuit permits a capacitor to sample and store the resultant strain gage output and the stored charge is used to modulate the successive intervals between pulses, each pulse producing an RF burst for transmission. FIGS. 8A, 8B, 8C and 8D show representative wave forms for points A, B, C and D in FIG. 6.

As described hereinabove, the transmitted RF pulses are received, decoded and demodulated by a receiver and demodulator system shown in FIG. 6 into a signal representing accelerations undergone by the ring 50. Amplitude and frequency of acceleration components as well as derived velocity components are all useful in predicting and detecting changes in activity and fatigue. The system may be used in numerous possible modes for extracting fatigue predictive indices. For example, separated frequency components can be used in a measurement of the short term acceleration activity to total activity so as to determine the amount of hand tremor. Separated acceleration amplitude signals can be used to generate a ratio which determines the slowing down of an individuals's activity so as to measure exhaustion. A velocity activity ratio can be used to show the slowing of movement and hence to indicate that an individual's ability to cope with control movements has diminished.

In additionn to detecting fatigue or other psychomotor manifestations, the invention can be used in numerous other areas such as in time and motion studies, analysis of bilateral distribution of manual workload, the location of infrequently used controls, and in medical and prosthetic applications.

In cases where transmission distance is considered more important than battery life, a frequency-modulated continuous wave signal could be transmitted instead of a pulse-time-modulated signal.

Although the invention has been described with respect to an exemplary embodiment thereof, it will be understood that variations and modifications can be effected in the embodiment without departing from the scope or spirit of the invention.

What is claimed is:

1. A miniaturized accelerometer telemetry system for monitoring the hand movements of a subject comprising:
   an accelerometer for detecting accelerational movements and for producing an electrical output signal in accordance therewith;
   transmitter means;
   modulator means for modulating the output of said transmitter with the output signal produced by said accelerometer;
   a housing, adapted to be worn on the person, for housing said accelerometer, said transmitter means and said modulator means;
   said accelerometer comprising an annular ring and a central support beam extending diametrically across said ring, a seismic mass affixed to said beam at the center of said ring so as to permit axial movements of said seismic mass, and first and second semiconductor strain gages, bonded to said beam on opposite sides of said mass, the electrical resistance of said gages varying in relationship to the stresses endured in each of said beams.

2. A miniaturized accelerometer telemetry system for monitoring the hand movements of a subject comprising:
   as accelerometer for detecting accelerational movements and for producing an electrical output signal in accordance therewith;
   transmitter means;
   modulator means for modulating the output of said transmitter with the output signal produced by said accelerometer;
   a housing, adapted to be worn on the person, for housing said accelerometer, said transmitter means and said modulator means;
   said modulator means comprising a sample-and-hold circuit connected to the output of said accelerometer, multivibrator means for pulsing said accelerometer and said sample-and-hold circuit, and amplifier means for connecting the output of said sample-and-hold circuit to the input of said multivibrator means; and
   said transmitter means comprising a pulse time modulation transmitter connected to an output of said multivibrator means.

3. A miniaturized accelerometer telemetry system for monitoring the hand movements of a subject comprising:
   an accelerometer for detecting accelerational movements and for producing an electrical output signal in accordance therewith;
   transmitter means;
   modulator means for modulating the output of said transmitter with the output signal produced by said accelerometer;
   a housing, adapted to be worn on the person, for housing said accelerometer, said transmitter means and said modulator means;
   said accelerometer including a seismic mass, a mount for said mass, and at least one strain gage for detecting the strain endured in said mount responsive to movements of said mass and for producing an output signal in accordance therewith;
   said modulator means comprising means for pulsing said at least one strain gage so as to produce a voltage proportional to the strain induced in said mount, means for storing said voltage, a constant current generator for producing an output that varies directly with the voltage stored by said storing means, an astable multivibrator for producing a pulse train of constant pulses, the interval between pulses in said pulse train being dependent on said output of said constant current generator; and
   said transmitter means comprising means for producing radio frequency pulses responsive to the output of said astable multivibrator.

4. An accelerometer telemetry transmission circuit comprising:
   an accelerometer for detecting accelerational movements and for producing an electrical output signal in accordance therewith;
   a sample-and-hold circuit connected to the output of said accelerometer;
   multivibrator means for pulsing said accelerometer and said sample-and-hold circuit, said multivibrator means including a control input connected to the output of said sample-and-hold circuit so that the output of said sample-and-hold circuit controls the interval between the pulses produced by said multivibrator means; and
   a transmitter means connected to an output of said multivibrator means.

5. An accelerometer telemetry transmission circuit as claimed in claim 4 wherein said accelerometer comprises first and second resistive strain gages electrically connected to form a voltage divider, a point on the junction between said strain gages being connected to the input to said sample-and-hold circuit.

6. An accelerometer telemetry transmission circuit as claimed in claim 4 wherein said transmitter means includes radio frequency oscillator means for producing radio frequency pulses having a variable interval therebetween, the duration of said interval being controlled by the output of said multivibrator means, said transmitter means further comprising a coil which serves as the inductive element of the tank circuit of said oscillator and as the radio frequency radiator of said transmitter means.

\* \* \* \* \*